United States Patent [19]
Aarnio et al.

[11] Patent Number: 5,417,223
[45] Date of Patent: May 23, 1995

[54] METHOD FOR FABRICATING INTRA-UTERINE CONTRACEPTIVES

[75] Inventors: Ari Aarnio; Keijo Heinonen, both of Helsinki, Finland

[73] Assignee: KMS MYYNTI, Bollsta, Finland

[21] Appl. No.: 923,962

[22] PCT Filed: Mar. 15, 1991

[86] PCT No.: PCT/FI91/00076

§ 371 Date: Sep. 16, 1992

§ 102(e) Date: Sep. 16, 1992

[87] PCT Pub. No.: WO91/13599

PCT Pub. Date: Sep. 19, 1991

[30] Foreign Application Priority Data

Mar. 16, 1990 [FI] Finland .................. 901310

[51] Int. Cl.⁶ .................................. A61F 5/46
[52] U.S. Cl. ........................ 128/833; 128/839
[58] Field of Search ............ 128/830, 831, 832, 833, 128/839, 885, 886, 834, 835, 836, 837, 838, 840, 841; 604/55, 44, 54; 606/19; 600/29, 30, 31

[56] References Cited

U.S. PATENT DOCUMENTS

| | | | |
|---|---|---|---|
| 4,198,966 | 4/1980 | Kaivola | 128/839 |
| 4,553,536 | 11/1985 | Chiozza | 128/833 |
| 4,562,835 | 1/1986 | Anderson | 128/839 |
| 4,628,924 | 12/1986 | Cimber | 128/839 |
| 4,715,365 | 12/1987 | Cimber | 128/840 |
| 4,775,149 | 10/1988 | Wilson . | |

FOREIGN PATENT DOCUMENTS

| | | |
|---|---|---|
| 0147274 | 11/1984 | European Pat. Off. . |
| 0292915 | 5/1988 | European Pat. Off. . |
| 0350087 | 6/1989 | European Pat. Off. . |
| 3209290 | 3/1981 | Germany . |
| 2079158 | 1/1982 | United Kingdom .......... 604/55 |
| 2230963 | 3/1990 | United Kingdom . |

OTHER PUBLICATIONS

Population Reports, Series B, No. 2, Jan. 1975.
Population Reports, Series B, No. 3, May 1979.

*Primary Examiner*—Robert A. Hafer
*Assistant Examiner*—David J. Kenealy
*Attorney, Agent, or Firm*—Kane, Dalsimer, Sullivan, Kurucz, Levy, Eisele & Richard

[57] ABSTRACT

The invention relates to a method of fabricating intra-uterine contraceptives, the said contraceptives comprising an elongated component (2), a copper wire spiral (3) placed around the elongated component (2) and a crosswise component (1) attached essentially by its middle point to one end of the elongated component (2). The elongated component (2) essentially of equal diameter throughout its length and the crosswise component (1) lateral to the elongated component (2) and attached to it by its midpoint are formed into a single contiguous piece. A separate copper wire spiral (3) is placed over the elongated component (2) via its unobstructed end, whereafter a sleeve (4) is then attached to support the copper wire spiral (3).

2 Claims, 1 Drawing Sheet

METHOD FOR FABRICATING INTRA-UTERINE CONTRACEPTIVES

This invention relates to a method for fabricating intra-uterine contraceptives.

Currently there are two kinds of copper-plastic spirals. One kind is formed of a contiguous shaft component and of a laterally outward extending crosswise component. The spiral component consists of copper wire wound around the elongated shaft component. The said method of fabrication is disadvantageous because the spiral component has to be separately wound over the shaft component. In addition, the copper wire spiral in the known solutions has been wound around the entire elongated shaft component in which cases, as is known, the copper around the base of the elongated shaft component does not possess an effective influence. The other kind of copper-plastic spirals have been designed to be such that their copper wire spiral extends only as far as the shaft component's upper half. This kind of a contraceptive is constructed in such a manner that the shaft component and the crosswise component are separate. The lower part of the shaft component is thicker than the upper part around which the copper wire spiral has been placed prior to assembling the contraceptive. In this way, the lower part of the shaft component and the union between the shaft component and the crosswise component hold the copper wire spiral in place. The latter kind of spiral is described in the FI patent publication 59719.

One disadvantage of the contraceptive in accordance with the said FI patent publication is that there is a connection between the shaft component and the crosswise component which, on the one hand, is difficult to implement and, on the other hand, may be susceptible to strain owing to its thinness. The arched locking component constitutes a protrusion which may be a cause of pain in the uterus. The design in accordance with the second implementation in the FI publication is intended to remedy this. The said solution does, however, make the crosswise component more complex in form.

The purpose of this invention is to provide an improvement to the above said disadvantages. This improvement is characterized in the main that the elongated component is essentially of equal diameter throughout its length and the crosswise component lateral to the elongated component and attached to it by its midpoint are formed into a single uniform piece and that a separate copper wire spiral is placed over the elongated component via its unobstructed end, whereafter a sleeve is then attached to support the copper wire spiral.

The main advantage of the invention is that it eliminates the need for the head required for the snap-on union between the crosswise component and the shaft component. As a result of this, the external diameter of the elongated component can be reduced, thereby enabling the diameter of the copper wire to be increased.

We shall now go on to describe the invention with references being made to the accompanying drawing, of which:

Figure 1:
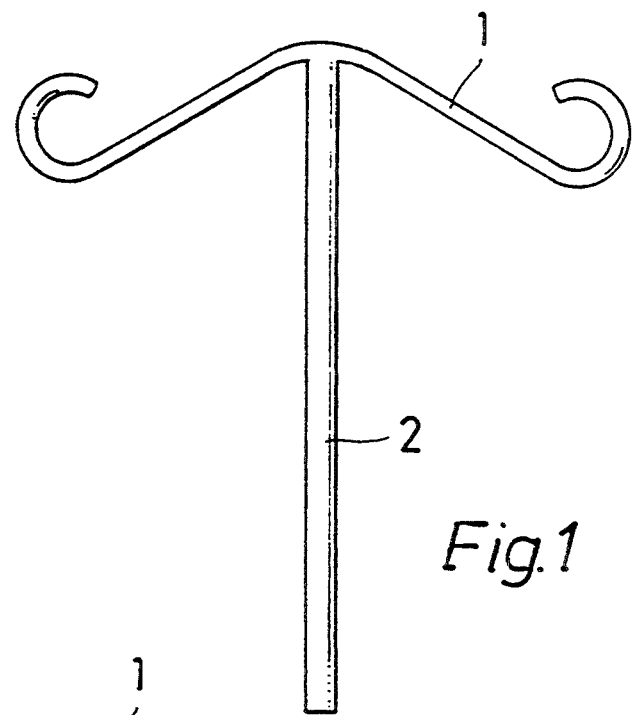
FIG. 1 is a side view of the elongated component and the crosswise oriented component.

With reference to FIG. 1, we shall now go on to describe the invention. In FIG. 1, 1 is the crosswise component, 2 is the elongated lengthwise component. In accordance with the method, the lengthwise and crosswise components, the said components constituting a contiguous piece, are fabricated first. The crosswise component is formed to be curved at both ends. The contiguous piece is formed in such a manner as to eliminate the occurrence of any sharp points or edges.

Figure 2:
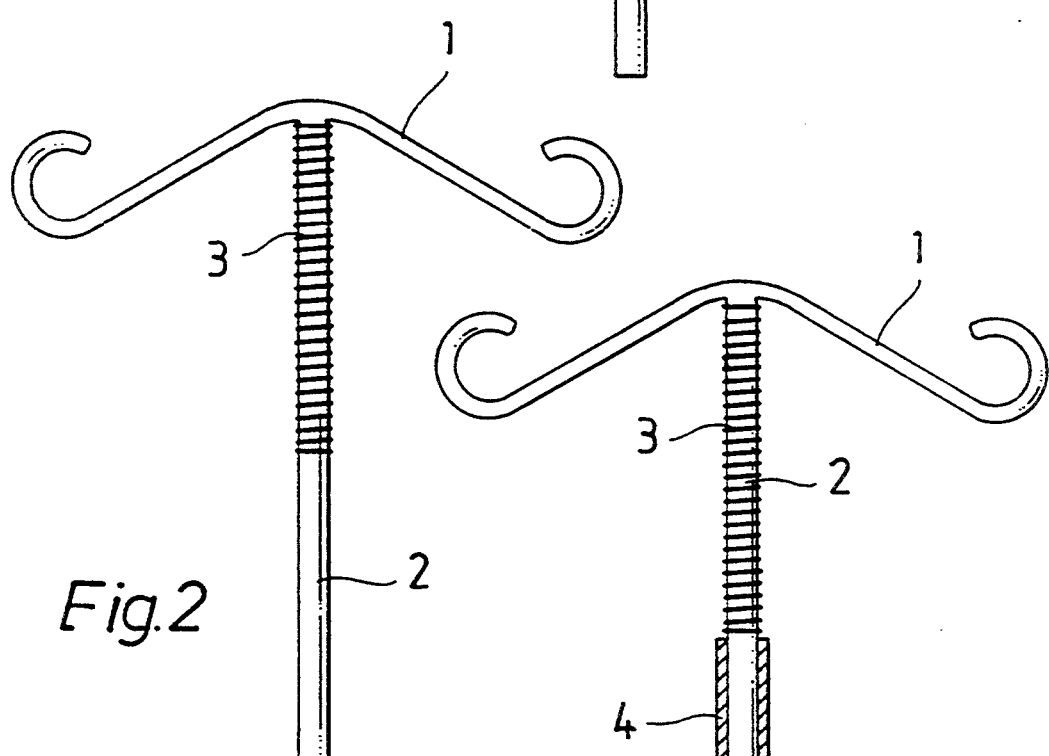
FIG. 2 is a side view like FIG. 1, but with the spiral included.

FIG. 2 shows the copper wire spiral, indicated by reference number 3, which is attached around the upper part of the lengthwise component. This spiral has been made into a spiral-like structure by means known to craftsmen. The thickness of the copper wire is that commonly used; e.g. 0.5 mm.

Figure 3:
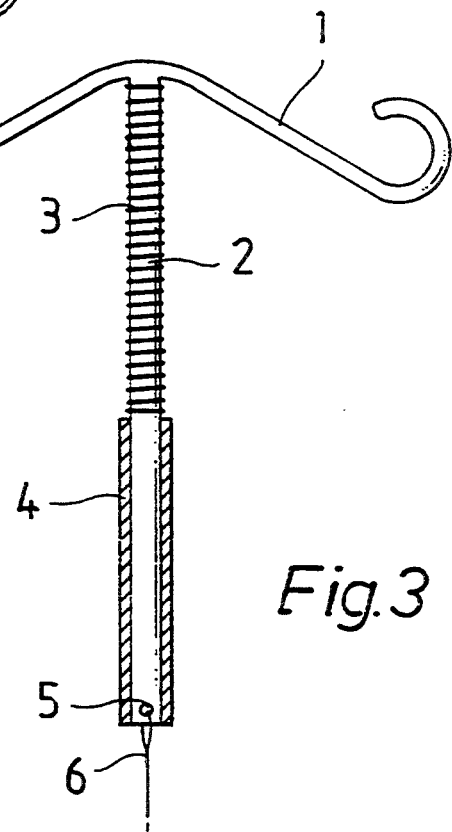
FIG. 3 is side view like FIG. 1, but with a sleeve included on the elongated- and crosswise components, the said sleeve having a hole bored into it for the purpose of attaching the sleeve to the elongated component.

FIG. 3 shows the contraceptive over whose elongated lower part a sleeve has been placed in such a manner that the said sleeve supports the copper wire spiral 3. The sleeve 4 has been provided with a hole 5 burnt through it for a string 6. The purpose in burning the hole is also to provide a lasting connection between the elongated component 2 and the sleeve 4 as a result of the melting and recooling of plastic in both the sleeve 4 and the elongated component 2.

The attaching of the sleeve to the elongated component 2 can be implemented, for instance, by means of a snap-on union, ultra-sonic treatment, heat treatment, etc. An advantageous way of joining sleeve 4 and the elongated component 2 is, however, by burning the above mentioned hole 5 into the sleeve.

The spiral is fabricated in accordance with the following stages:

A) An uniform piece, comprising an elongated component and a component oriented crosswise to the elongated component and joined to one end of it and possessing symmetrically curved ends, is formed.

B) A ready-to-use copper wire spiral is placed over the elongated component via the unobstructed other end of the elongated component formed in the previous stage.

C) A sleeve is inserted to provide support for the copper wire spiral via the same end as the spiral. A hole is then burnt through that end of the sleeve which is opposite the end in contact with the spiral for the purpose of slipping a string into the hole and to fasten the sleeve firmly over the elongated component.

It is also possible to make such a hole through the sleeve as will also pass through the elongated component. When this is done, it may be that these components are attached to one another only by means of the string.

The copper wire spiral can be replaced by other materials with contraceptive properties such as enzymes or other materials made of other substances. In the case of enzymes, the contraceptive substance may, for example, be tubular or rod-like in form when fabricated.

We have described the invention with reference being made to only one of its advantageous implementation examples. It is, nevertheless, clear to a craftsman in the particular line of industry that the method in accordance with the invention can be implemented in the fabrication of contraceptives differing in outward shape, such as T-shaped spirals. All modifications within the inventive idea defined by the patent claims are, naturally, possible.

We claim:

1. A method of fabricating intra-uterine contraceptives, comprising the steps of:

forming a single uniform piece having an elongated component having a free end and being essentially of equal diameter throughout its length and a crosswise component having a midpoint and being lateral to the elongated component so that said crosswise component is attached to said elongated component by its midpoint;

placing a separate contraceptive member over said elongated component via its free end; and introducing a sleeve via said free end over said elongated component to support the contraceptive member;

burning a hole into said sleeve to achieve the connection between said sleeve and said elongated component and burning a part of said elongated component which upon cooling forms a firm connection between said elongated component and sleeve.

2. A method as claimed in claim 1, including the step of burning the hole also in the elongated member and ensuring the connection between said sleeve and said elongated component by inserting a block, string or a rivet in the hole.

* * * * *